(12) United States Patent
Warnack et al.

(10) Patent No.: US 7,322,959 B2
(45) Date of Patent: Jan. 29, 2008

(54) BALLOON CATHETER WITH RADIOOPAQUE MARKER

(75) Inventors: Boris Warnack, Mountain View, CA (US); Suk-Woo Ha, Marthalen (CH)

(73) Assignee: Abbott Laboratories Vascular Enterprises, Limited, Dublin (IE)

( * ) Notice: Subject to any disclaimer, the term of this patent is extended or adjusted under 35 U.S.C. 154(b) by 0 days.

(21) Appl. No.: 10/523,897

(22) PCT Filed: Jul. 31, 2003

(86) PCT No.: PCT/EP03/08493

§ 371 (c)(1), (2), (4) Date: Sep. 19, 2005

(87) PCT Pub. No.: WO2004/014475

PCT Pub. Date: Feb. 19, 2004

(65) Prior Publication Data

US 2006/0129045 A1    Jun. 15, 2006

(30) Foreign Application Priority Data

Aug. 6, 2002  (EP) .................................. 02017547

(51) Int. Cl.
*A61M 29/00* (2006.01)

(52) U.S. Cl. .................. 604/103.1; 606/194; 623/1.11

(58) Field of Classification Search ............. 604/96.01, 604/103.09, 103.1; 606/192, 194; 623/1.11
See application file for complete search history.

(56) References Cited

U.S. PATENT DOCUMENTS

| | | | | | |
|---|---|---|---|---|---|
| 4,938,220 | A | * | 7/1990 | Mueller, Jr. | 600/435 |
| 5,484,409 | A | * | 1/1996 | Atkinson et al. | 604/103.03 |
| 5,547,472 | A | * | 8/1996 | Onishi et al. | 604/103.01 |
| 5,799,731 | A | * | 9/1998 | Avakov et al. | 166/77.2 |
| 6,129,708 | A | * | 10/2000 | Enger | 604/103.04 |
| 6,500,147 | B2 | * | 12/2002 | Omaleki et al. | 604/103.09 |
| 6,520,934 | B1 | * | 2/2003 | Lee et al. | 604/103.1 |
| 2002/0007146 | A1 | * | 1/2002 | Omaleki et al. | 604/103.09 |
| 2003/0105426 | A1 | * | 6/2003 | Jorgensen | 604/103.1 |
| 2003/0176837 | A1 | * | 9/2003 | Fitzmaurice et al. | 604/103.04 |

FOREIGN PATENT DOCUMENTS

EP    0 597 506    * 10/1989

* cited by examiner

*Primary Examiner*—LoAn H. Thanh
(74) *Attorney, Agent, or Firm*—Michael J. DeHaemer, Jr.; Luce, Forward, Hamilton & Scripps LLP

(57) ABSTRACT

In order to enhance the flexibility and trackability of a catheter (1) that is particularly adapted for use in delivering a stent (5), the catheter (1) comprises a marker arrangement (7, 8) that includes at least one marker (10, 11) made from a wire of a highly radiopaque and ductile material. Said wire is preferably wrapped around a second inner tube (2) of the catheter (1).

17 Claims, 2 Drawing Sheets

BALLOON CATHETER WITH RADIOOPAQUE MARKER

The present invention concerns a catheter, in particular for use in delivering a stent, according to the preamble part of claim 1.

Such a catheter is known from WO 98/07390. The known catheter in the form of a stent delivery system comprises short solid marker bands made from a radiopaque material. These marker bands constitute solid tubes. The drawback of these tubes is the increase of profile of the balloon and, even more important, the resulting rigid length of between 1 mm to 1.2 mm what, in turn, results in a reduction of the flexibility of the catheter tube. Therefore, the known catheter, when pushed forward through a curved vessel, suffers from the drawback of an undesired stiffness in the region of the marker bands diminishing especially the trackability of the catheter. Finally, this stiffening of the catheter tube results in a certain danger of buckling of the catheter.

It is therefore an object underlying the present invention to provide a catheter according to the preamble part of claim 1, overcoming the beforementioned drawbacks of the prior art and providing a marker arrangement of a high X-ray visibility along with a sufficient flexibility and trackability of the catheter.

The solution of this object is achieved by the features of claim 1.

The provision of markers being made of a wire of a highly radiopaque and ductile material reduces the rigid length of the markers as the wire provides higher flexibility and also less profile.

Therefore, the catheter according to the present invention provides a high flexibility and trackability and, simultaneously, the indication of the length of the cylindrical part of the balloon or the length of a stent mounted on the balloon is ensured by the highly radiopaque and ductile material of the wire-markers.

The dependent claims contain advantageous embodiments of the present invention.

The specifically advantageous embodiment of the catheter according to the present invention provides for a wire that is wrapped around the inner tube and preferably at least partly embedded in the tube material.

Furthermore, it is possible to build up different kinds of wire arrangements, especially the wire arrangement of a plurality of at least partly overlapping layers what enhances the radiopaqueness even more.

Preferred diameters of the wire of the marker according to the present invention are 0.01, 0.02 and/or 0.04 mm.

The free ends of the wire can be fixed either mechanically or by using an adhesive bonding.

The wire can have various kinds of cross-sectional configurations, preferably circular or flat and rectangular cross-sections.

Moreover, it is possible to cover the wrapped wire with an additional thin tube-like cover.

Claim 9 defines a marker according to the present invention, adapted to be used in a catheter according to the preamble portion of claim 1.

Figure 1:
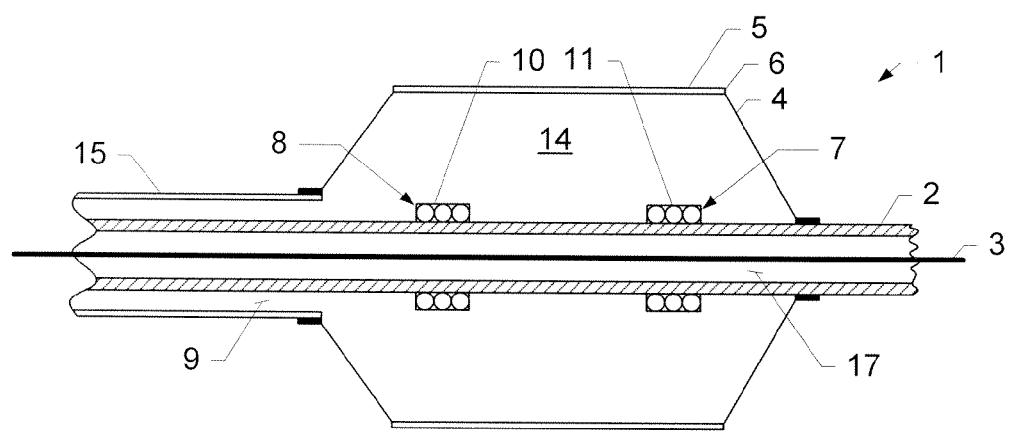
Figure 2:
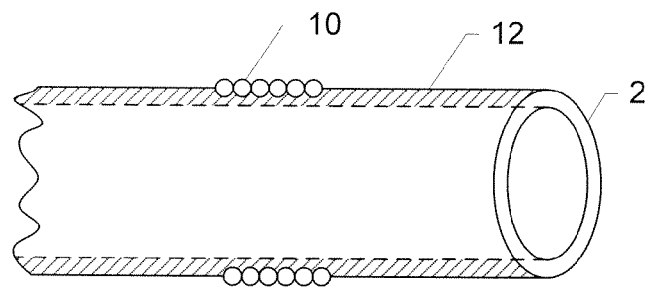
Figure 3:
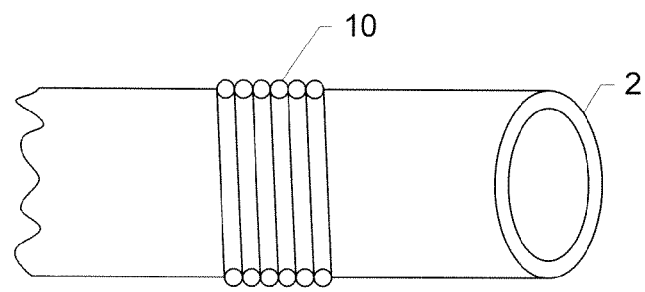
Figure 4:
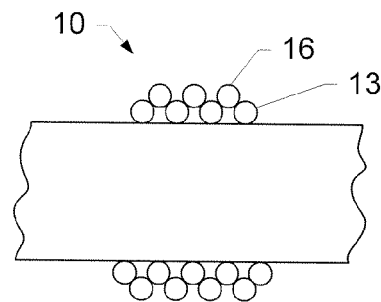
Figure 5:
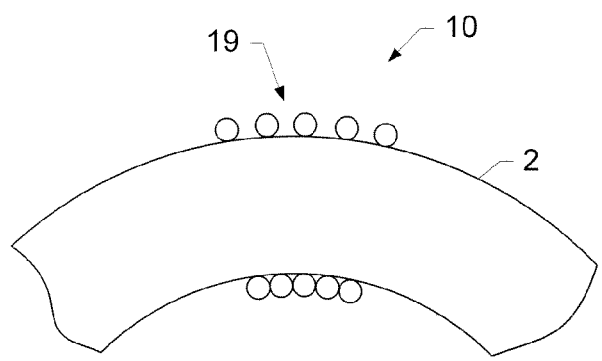
Figure 6:
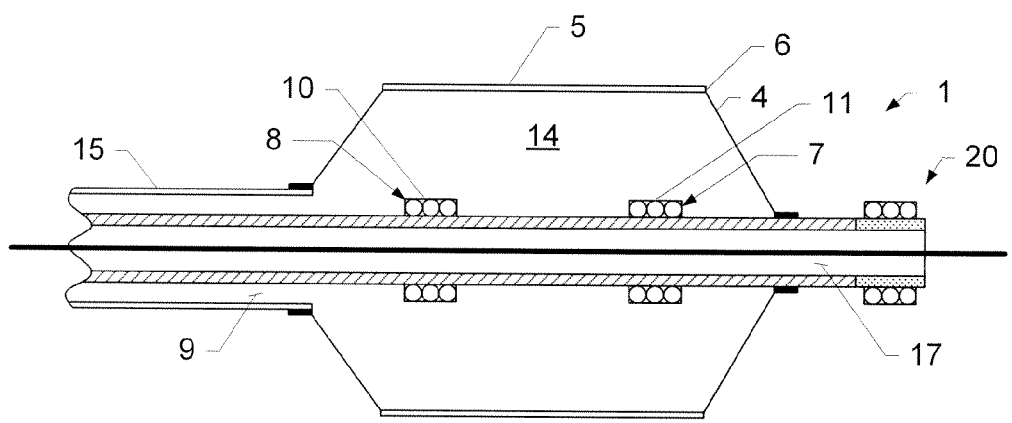

The following is a description of some specific embodiments of the present invention, reference being made to the accompanying drawings, in which FIG. 1 is a schematically simplified view of the distal end of a catheter according to the present invention, FIGS. 2 to 4 are different marker arrangements according to the present invention, and FIG. 5 is a cross-sectional view of the preferred catheter marker arrangement of FIG. 2, during bending of the catheter tube; and FIG. 6 is a cross sectional view of the distal end of a catheter having a marker at a tip thereof.

FIG. 1 depicts a catheter 1 that is particularly adapted for use in delivering a stent 5 disposed on an exterior surface 6 of a balloon 4 of catheter 1.

Balloon 4 is sealingly connected to a first tube 15 adjacent to the distal end of the balloon. The balloon 4 defines an interior volume 14 that is in communication with a first lumen 9 of the first outer tube 15. So, e.g. a heated fluid can be introduced through the proximal end of the first lumen 9 in order to pressurize the balloon 4 and to heat the stent engagement region 6.

FIG. 1, furthermore, displays a second inner tube 2 that, for the depicted embodiment, is disposed concentrically within the first outer tube 15. This second inner tube 2 defines a second inner lumen 17 for a guidewire 3.

Finally, the catheter 1 comprises a marker arrangement 7, 8 that is disposed on the second inner tube 3 within interior volume 14 of balloon 4.

The preferred embodiment of the catheter shown in FIG. 1 comprises two markers 10, 11, constituting the marker arrangement 7, 8 and being made from a wire of a highly radiopaque and ductile material.

FIG. 2 shows a part of the second inner tube 2 with the marker 10 being partly embedded within the wall material 12 of tube 2. Basically, the wire of marker 10 can also be totally embedded in material 12 of the wall of the second inner tube 2.

FIG. 3 depicts also part of second inner tube 2 showing a coil-like marker 10 that can also be embedded partly or totally within the material 12 of the tube wall.

FIG. 4 shows a particularly advantageous embodiment of the marker 10 (or, of course, also of marker 11) comprising two layers 13, 16 of partly overlapping wires.

FIG. 5 depicts tube 2 in a bent state. The inner part 18 of the wire marker 10 or 11 is compressed in this state while the outer part 19 of marker 10 is expanded thus ensuring a higher flexibility and trackability of the catheter 1 according to the present invention.

Moreover, the before-explained catheter 1 may comprise a catheter tip being equipped with one marker. This arrangement can secure the visibility of the catheter tip and can be used with balloon catheters, aspiration catheters, guide catheters, angiographic catheters, imaging catheters, and in general with any kind of catheter.

According to one embodiment, catheter 1 may comprise catheter tip 20 equipped with marker 21, as shown in FIG. 6. This arrangement can secure the visibility of the catheter tip and can be used with balloon catheters, aspiration catheters, guide catheters, angiographic catheters, imaging catheters, and in general with any kind of catheter. The positioning of the marker according to the preset invention at the catheter tip enhances the flexibility and the softness of the catheter tip to prevent the wall of the body vessels from being injured.

Moreover, the high flexibility results in an improved trackability of the entire catheter according to the present invention.

The invention claimed is:

1. A catheter for delivering a stent, comprising:
an outer tube having a proximal end, a distal end and a wall defining a lumen;

a balloon sealingly connected to the outer tube adjacent the distal end, the balloon defining an interior volume and having an exterior surface;

an inner tube disposed within the outer tube and defining a lumen for a guidewire; and a marker arrangement comprising at least one marker made from a wire of a highly radiopaque and ductile material wrapped around the inner tube in a plurality of at least partially overlapping layers to form a coil-like marker that is flexible along a longitudinal axis of the inner tube.

2. The catheter of claim 1, wherein the wire is at least partially embedded in the material of the inner tube.

3. The catheter of claim 1, wherein the wire is covered by a thin tube-like cover.

4. The catheter of claim 1, wherein the wire has a circular cross-section.

5. The catheter of claim 1, wherein the wire has a flat, rectangular cross-section.

6. The catheter of claim 1, wherein the wire is made out of a material selected from the group of platinum, tantalum, gold and alloys of these materials.

7. The catheter of claim 1, wherein the marker arrangement is disposed on the inner tube within the balloon.

8. The catheter of claim 1, wherein at least one marker is disposed at the catheter tip.

9. A catheter for delivering a stent, comprising:

an outer tube having a proximal end, a distal end and a wall defining a lumen;

an inner tube disposed within the outer tube and defining a lumen for a guidewire;

a balloon sealingly connected to the inner tube and the outer tube near the distal ends thereof, the balloon defining an interior volume and having an exterior surface; and a marker made from a wire of a highly radiopaque and ductile material, wherein the wire is wrapped in a plurality of at least partially overlapping layers such that the marker is flexible along a length of the catheter.

10. The catheter of claim 9, wherein the wire is wrapped around the inner tube to form a coil-like marker tube.

11. The catheter of claim 9, wherein the wire is at least partially embedded in the material of the inner tube.

12. The catheter of claim 9, wherein the wire is covered by a thin tube-like cover.

13. The catheter of claim 9, wherein the wire has a circular cross-section.

14. The catheter of claim 9, wherein the wire has a flat, rectangular cross-section.

15. The catheter of claim 9, wherein the wire is made out of a material selected from the group of platinum, tantalum, gold and alloys of these materials.

16. The catheter of claim 9, wherein the marker arrangement is disposed on the inner tube within the balloon.

17. The catheter of claim 9, wherein the at least one marker is disposed at the catheter tip.

* * * * *